United States Patent
Zeng et al.

(10) Patent No.: US 12,268,870 B2
(45) Date of Patent: Apr. 8, 2025

(54) MICROELECTRODE, PREPARATION METHOD THEREOF AND NEURAL PROSTHESIS

(71) Applicant: SHENZHEN INSTITUTES OF ADVANCED TECHNOLOGY, Guangdong (CN)

(72) Inventors: Qi Zeng, Guangdong (CN); Tianzhun Wu, Guangdong (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 829 days.

(21) Appl. No.: 17/251,002

(22) PCT Filed: Jul. 9, 2019

(86) PCT No.: PCT/CN2019/095263
§ 371 (c)(1),
(2) Date: Dec. 10, 2020

(87) PCT Pub. No.: WO2021/003670
PCT Pub. Date: Jan. 14, 2021

(65) Prior Publication Data
US 2021/0260368 A1 Aug. 26, 2021

(51) Int. Cl.
*A61N 1/05* (2006.01)
*A61N 1/36* (2006.01)
*H01B 1/02* (2006.01)

(52) U.S. Cl.
CPC .............. *A61N 1/0551* (2013.01); *A61N 1/05* (2013.01); *A61N 1/3605* (2013.01); *H01B 1/02* (2013.01)

(58) Field of Classification Search
CPC ...... A61N 1/0551; A61N 1/05; A61N 1/3605; H01B 1/02
See application file for complete search history.

(56) References Cited

U.S. PATENT DOCUMENTS 7,676,274 B2 * 3/2010 Hung .................. A61N 1/0526
607/116
2003/0047450 A1 3/2003 Yang et al.
(Continued)

FOREIGN PATENT DOCUMENTS

CN 101172184 A 5/2008
CN 104548335 A 4/2015
(Continued)

OTHER PUBLICATIONS

The First Office Action issued in corresponding CN Application No. CN201910615257.0, mailed Oct. 17, 2022.
(Continued)

*Primary Examiner* — Pamela M. Bays
(74) *Attorney, Agent, or Firm* — HAUPTMAN HAM, LLP

(57) ABSTRACT

The present invention provides a microelectrode, comprising a flexible layer, an electrically conductive layer and a plurality of platinum dendrite structures, wherein the electrically conductive layer is arranged in the flexible layer, and wherein on the surface of the flexible layer are a plurality of grooves within which the electrically conductive layer is revealed partially, and wherein each of the groove is provided with one platinum dendrite structure therein. The plurality of grooves serve as focal electrodes distributed uniformly, with smaller electrode sites and more recording points. The modified platinum dendrite structures increase the surface area, electrical performance, biocompatibility and service life of the microelectrode. Besides, creating virtual electrodes by current steering technique increases the number of stimuli received by microelectrode during use, and improves its resolution in applications.

5 Claims, 4 Drawing Sheets

(56) References Cited

U.S. PATENT DOCUMENTS

| | | | |
|---|---|---|---|
| 2007/0224244 A1* | 9/2007 | Weber | A61L 27/047 424/426 |
| 2009/0177144 A1* | 7/2009 | Masmanidis | A61B 5/291 600/378 |
| 2010/0221635 A1* | 9/2010 | Yamada | H01M 8/1004 216/13 |
| 2016/0012310 A1* | 1/2016 | Kozicki | G06K 19/086 382/218 |
| 2017/0232251 A1 | 8/2017 | Neysmith et al. | |
| 2018/0248200 A1* | 8/2018 | Arihara | H01M 4/92 |

FOREIGN PATENT DOCUMENTS

| | | |
|---|---|---|
| CN | 106646048 A | 5/2017 |
| CN | 108652618 A | 10/2018 |
| CN | 108853717 A | 11/2018 |
| CN | 109205551 A | 1/2019 |
| CN | 109700453 A | 5/2019 |

OTHER PUBLICATIONS

International Search Report issued in corresponding International Application No. PCT/CN2019/095263, mailed April 9. 2020, pp. 1-5, State Intellectual Property Office of the P.R. China, Beijing, China.

* cited by examiner

MICROELECTRODE, PREPARATION METHOD THEREOF AND NEURAL PROSTHESIS

RELATED APPLICATION

The present application is a National Phase of International Application No. PCT/CN2019/095263, filed Jul. 9, 2019.

FIELD OF THE INVENTION

The invention relates to the field of biomedical engineering, in particular to microelectrode, preparation method thereof, and neural prosthesis.

BACKGROUND OF THE INVENTION

As one of the most important implantable micro-devices, nerve electrodes are used to stimulate nerve tissue or record nerve electrical signals, and are widely used in the field of life sciences such as neurophysiology and brain science research. However, with the increasing requirements for accuracy of stimulation or recording, neural electrodes with low density and simple functions no longer meet the demand for precise regulation. Neural electrodes are developing towards integration and miniaturization. Therefore, the reduced size of microelectrodes causes performance problems such as increased electrode impedance and reduced capacitance, which limits their clinical applications. As a result, people are striving to develop a neural electrode, which has multi-focus electrodes in a limited space to balance the number of electrodes and electrode spacing and break through its limiting spatial resolution, and which reduces the critical stimuli charge density by increasing actual area of electrode through surface modification in the case of fixed electrode geometry, while increasing the number of perceptions and improving resolution.

SUMMARY OF THE INVENTION

In order to solve the above problems, the present invention provides a microelectrode comprising a flexible layer, an electrically conductive layer and a plurality of platinum dendrite structures, wherein the electrically conductive layer is arranged in the flexible layer, wherein on the surface of the flexible layer are a plurality of grooves within which the electrically conductive layer is revealed partially, and wherein each of the groove is provided with one platinum dendrite structure therein. The plurality of grooves serve as focal electrodes distributed uniformly, with smaller electrode sites and more recording points. The modified platinum dendrite structures increase the surface area, electrical performance, biocompatibility and service life of the microelectrode. Besides, creating virtual electrodes by current steering technique increases the number of stimuli received by microelectrode during use, and improves its resolution in applications.

In a first aspect, the present invention provides a microelectrode comprising a flexible layer, an electrically conductive layer and a plurality of platinum dendrite structures,
wherein the electrically conductive layer is arranged in the flexible layer, and
wherein on the surface of the flexible layer are a plurality of grooves within which the electrically conductive layer is revealed partially, and
wherein each of the groove is provided with one platinum dendrite structure therein.

Alternatively, the flexible layer has a thickness of 3 µm-300 µm. Further, the flexible layer has a thickness of 10 µm-260 µm. In the present invention, material of the flexible layer can be, but is not limited to, polyimide or parylene.

Alternatively, the electrically conductive layer has a thickness of 0.1 µm-100 µm. Further, the electrically conductive layer has a thickness of 0.5 µm-80 µm.

Alternatively, a distance between adjacent grooves is in a range of 10 µm-1000 µm. Further, the distance between adjacent grooves is in a range of 50 µm-700 µm. Furthermore, the distance between adjacent grooves is in a range of 80 µm-500 µm. In the present invention, the distance between adjacent grooves is selected to be beneficial to the creation of virtual electrode channels, thereby increasing the number of perceptions of the microelectrode during use, and thus promoting resolution.

Alternatively, the plurality of the grooves are arranged in an array. The array arrangement of the grooves is beneficial to the array arrangement of the platinum dendrite structure arranged in the grooves, thereby increasing the number of virtual channels created by the microelectrode and increasing the number of stimuli.

In the present invention, a shape of an opening of the groove can be, but is not limited to, a circle, a square, a rectangle, an ellipse, a diamond, or an irregular shape.

Alternatively, the groove has a depth of is 0.5 µm-80 µm. Further, the groove has a depth of 2 µm-70 µm.

Alternatively, a distribution density of the grooves in the microelectrode is in a range of 10-300 grooves/cm². Further, the distribution density of the grooves in the microelectrode is in a range of 50-200 grooves/cm².

Alternatively, the platinum dendrite structure consists of a plurality of platinum dendrites. Further, the platinum dendrite comprises at least one of platinum nanowires, platinum nanorods, platinum nanocones, and platinum nanoflowers. In the present invention, the platinum dendrite structures greatly increase the surface area of the microelectrode, thereby improving its electrical performance.

Alternatively, the platinum nanowires have a diameter of 2 nm-50 nm and a length of 0.2 µm-5 µm. Further, the platinum nanowires have a diameter of 3 nm-9 nm and a length of 1.2 µm-4 µm.

Alternatively, the platinum nanorods have a diameter of 0.1 µm-1 µm and a length of 0.3 µm-5 µm. Further, the platinum nanorods have a diameter of 0.15 µm to 0.85 µm and a length of 0.8 µm to 4 µm.

Alternatively, the bottom of the platinum nanocones has a diameter of 0.1 µm-1 µm, and the platinum nanocones have a height of 0.3 µm-5 µm. Further, the bottom of the platinum nanocones has a diameter of 0.2 µm-0.95 µm, and the platinum nanocones have a length of 1.5 µm-3.5 µm.

Alternatively, the platinum nanoflowers have an average diameter of 0.2 µm-3 µm. Further, the platinum nanoflowers have an average diameter of 0.5 µm-2.6 µm. Further, each of the platinum nanoflowers comprises a plurality of platinum nanosheets, and the platinum nanosheets have a lateral dimension of 0.1 µm-1 µm. Furthermore, the platinum nanosheets have a lateral dimension of 0.15 µm-0.8 µm.

In the present invention, the platinum nanowires, platinum nanorods, and platinum nanocones are selected to be beneficial to further increase the surface area of the microelectrode and improve its electrical performance.

Alternatively, a distribution density of the platinum dendrites in the platinum dendrite structure is in a range of 10 pcs/µm²-300 pcs/µm². Further, the distribution density of the platinum dendrites in the platinum dendrite structure is in a range of 25 pcs/$\mu m^2$-265 pcs/$\mu m^2$. Furthermore, the distribution density of the platinum dendrites in the platinum dendrite structure is in a range of 50 pcs/$\mu m^2$-180 pcs/$\mu m^2$. In the present invention, the denser distribution of platinum dendrites will enable the microelectrode to have a larger surface area, thereby greatly improving the electrical performance and being more beneficial to its application.

Alternatively, the platinum dendrite structure has a thickness of 0.3 µm-70 µm. Further, the platinum dendrite structure has a thickness of 3 µm-60 µm. Furthermore, the platinum dendrite structure has a thickness of 5 µm-50 µm. In the present invention, the thickness of the platinum dendrite structure is selected to be beneficial to the generation and transmission of stimuli.

In the present invention, the thickness of the platinum dendrite structure may be equal to the depth of the groove, or less than the depth of the groove, or greater than the depth of the groove. In the embodiment where the thickness of the platinum dendrite structure is greater than the depth of the groove, the surface area of the microelectrode is further increased, thereby improving electrical performance of the microelectrode.

Alternatively, a plurality of the platinum dendrite structures are arranged in an array such that an array of platinum dendrite structures is formed on the microelectrode, that is, a microelectrode array is formed. This arrangement further improves the overall electrical performance of the microelectrode and the number of stimuli received during use, increasing the number of virtual channels and promoting its resolution in applications.

In the present invention, the platinum dendrite structure may completely cover the bottom of the groove (that is, the surface of the electrically conductive layer revealed in each groove), or partially cover the bottom of the groove.

Alternatively, an electrically conductive polymer layer is arranged on the platinum dendrite structure. The electrically conductive polymer layer is a soft material with excellent biocompatibility and good electrical properties, enabling it to fit tissues, reduce immune responses, and improve the long-term safety of microelectrode. Therefore, an electrically conductive polymer layer is arranged on the platinum dendrite structure to combine "hard and soft material" to further improve the biocompatibility and service life of the microelectrode. In the present invention, the electrically conductive polymer layer may be arranged on all or some platinum dendrite structures. Further, in an embodiment where the electrically conductive polymer layer is arranged on all platinum dendrite structures, the biocompatibility and stability of the microelectrode is further improved.

Alternatively, the electrically conductive polymer layer has a thickness of 0.1 µm-20 µm. Further, the electrically conductive polymer layer has a thickness of 2 µm-16 µm. In the present invention, the thickness of the electrically conductive polymer layer is selected to be beneficial to the transmission of stimuli of the electrically conductive polymer layer and the platinum dendrite structure.

Alternatively, the material of the electrically conductive polymer layer comprises at least one of polypyrrole, polyaniline, polythiophene and its derivatives, and electrically conductive hydrogel. That is, the material of the electrically conductive polymer layer comprises at least one of polypyrrole, polyaniline, polythiophene, polypyrrole derivatives, polyaniline derivatives, polythiophene derivatives and electrically conductive hydrogel. In the present invention, the material of the electrically conductive polymer layer is selected to be beneficial to the biocompatibility of the electrically conductive polymer layer, thereby improving the biocompatibility and safety of the microelectrode.

In the microelectrode provided by the first aspect of the present invention, the revealed electrically conductive layer and the platinum dendrite structure serve as a plurality of electrodes distributed uniformly, with smaller electrode sites and more electrodes and recording points, which brings intensive stimuli to nerve and overcomes the disadvantage of an ordinary planar electrode that the electrical lines of force diverge due to stronger edge electric field than the center electric field. The platinum dendrite structures increase the surface area of the microelectrode and effectively improve the electrochemical performance of the microelectrode, such as reduced impedance, lower critical stimulating charge density, improved charge storage capacity and charge injection capacity, etc. Further, the platinum dendrite structures are well combined with the electrically conductive layer, avoiding the shedding of the platinum dendrite structures and improving the biocompatibility and service life of the microelectrode. Besides, creating virtual electrodes by current steering technique increases the number of stimuli received by microelectrode during use, and improves its resolution in applications. Using current steering technique, the electric fields of adjacent electrodes interact in space to generate additional, perceptible, virtual stimuli between the stimuli produced by the two electrodes alone, that is, creating virtual electrode channels. This increases the number of stimuli received by microelectrode during use, and improves its resolution in applications, thereby broadening the application of microelectrode.

In a second aspect, the present invention provides a method for preparing a microelectrode, comprises:
  providing a substrate and preparing a first flexible layer on the substrate;
  preparing an electrically conductive layer on the first flexible layer through a mask;
  depositing a second flexible layer on the electrically conductive layer such that the second flexible layer partially covers the surface of the electrically conductive layer and partially covers the surface of the first flexible layer;
  etching the second flexible layer to reveal partially the electrically conductive layer, and forming a plurality of grooves;
  removing the substrate and depositing platinum dendrite structures in the plurality of grooves to obtain a microelectrode.

Alternatively, the substrate may be, but is not limited to, a silicon wafer, a silicon oxide wafer or a glass wafer.

Alternatively, the step of preparing a first flexible layer on the substrate comprises performing spin coating or deposition to prepare the first flexible layer on the substrate.

Alternatively, the step of preparing an electrically conductive layer on the first flexible layer through a mask comprises disposing a mask over the first flexible layer, and forming the electrically conductive layer on the first flexible layer by deposition such that the electrically conductive layer partially covers the first flexible layer. Further, the deposition may be, but is not limited to, physical vapor deposition or chemical vapor deposition.

Alternatively, the material of the first flexible layer and the second flexible layer may be, but is not limited to, polyimide or parylene.

Alternatively, the etching comprises at least one of dry etching and wet etching. Specifically, the etching may be, but is not limited to, reactive ion etching or plasma etching.

Alternatively, the step of depositing platinum dendrite structures in the plurality of grooves comprises: providing a platinum salt solution, performing constant potential deposition or constant current deposition to form the platinum dendrite structures in the plurality of grooves.

Further, the platinum salt comprises at least one of platinum chloride, ammonium hexachloroplatinate, potassium hexachloroplatinate, sodium hexachloroplatinate, chloroplatinic acid, platinum nitrate, platinum sulfate, potassium tetrachloroplatinate and ammonium tetrachloroplatinate.

Further, the platinum salt solution has a concentration of 30 mmol/L or more. Furthermore, the platinum salt solution has a concentration of 35 mmol/L or more. A high-concentration platinum salt solution (greater than 30 mmol/L) is used in the present invention to prepare platinum dendrite structures, further increasing the surface area of the microelectrode while greatly increasing its electrochemical performance, so that it has an improved charge storage capacity and charge injection capacity, etc.

Further, the platinum salt solution has a pH of 7-8. Furthermore, the platinum salt solution has a pH of 7.2-7.6. The pH of the platinum salt solution in such range is beneficial to the deposition of the platinum dendrite structure and uniform structure of the platinum dendrite structure.

Further, the method further comprises pretreating the grooves, before performing constant potential deposition or constant current deposition to form the platinum dendrite structures in the plurality of grooves. Further, the step of pretreating comprises cleaning and roughening the grooves. Pretreatment on the grooves will improve the bonding between the grooves and platinum dendrite structure subsequently deposited therein such that the platinum dendrite structure will not readily fall off the grooves.

Further, the constant potential deposition may be performed at a potential of −0.6V to −0.75V for 20 min to 60 min. Further, the constant potential deposition may be performed at a potential of −0.7V to −0.73V for 30 min to 60 min.

Further, the constant current deposition may be performed at a current of −2 μA to −5 μA for 20 min to 60 min. Further, the constant current deposition may be performed at a current of −3.5 μA to −4.5 μA for 30 min to 60 min.

The constant potential deposition/constant current deposition is performed under the selected condition to be beneficial to prepare a platinum dendrite structure with uniform structure, and increase the surface area of the platinum dendrite structure, thereby increasing the surface area of the microelectrode and improving its electrical performance.

Alternatively, the method further comprises depositing an electrically conductive polymer layer on the platinum dendrite structure in-situ or through a template, after depositing platinum dendrite structures in the plurality of grooves. In the present invention, deposition of the electrically conductive polymer layer is beneficial to the biocompatibility of the electrically conductive polymer layer, thereby improving the biocompatibility and safety of the microelectrode.

The method for preparing microelectrode provided by the second aspect of the present invention is simple to operate, suitable for a large-scale preparation of microelectrode with uniform and stable performance.

In a third aspect, the present invention provides a neural prosthesis, which comprises a microelectrode as defined in the first aspect or as manufactured by the method described in the second aspect.

In the present invention, the neural prosthesis can be, but is not limited to, a cochlear implant, an optic nerve prosthesis, an implantable cardiac pacemaker or an implantable deep brain stimulator, especially an optic nerve prosthesis. The microelectrode in the neural prosthesis can realize precise and dynamic nerve stimuli and improve the performance of the neural prosthesis. Specifically, when used in optic nerve prostheses, microelectrode can increase the number of received stimuli and produce higher spatial resolution.

In the present invention, the neural prosthesis comprises one or more of the microelectrodes. Specifically, in an embodiment where the neural prosthesis comprises a plurality of the microelectrodes, the plurality of the microelectrodes are arranged in an array.

In summary, the present invention provides the following advantages.

Firstly, in the microelectrode provided by the present invention, the revealed electrically conductive layer and the platinum dendrite structure serve as a plurality of electrodes distributed uniformly, with smaller electrode sites and more electrodes and recording points, which brings intensive stimuli to nerve and overcomes the disadvantage of an ordinary planar electrode that the electrical lines of force diverge due to stronger edge electric field than the center electric field. The platinum dendrite structures increase the surface area of the microelectrode and effectively improve the electrochemical performance of the microelectrode, such as reduced impedance, lower critical stimulating charge density, improved charge storage capacity and charge injection capacity, etc. Further, the platinum dendrite structures are well combined with the electrically conductive layer, avoiding the shedding of the platinum dendrite structures and improving the biocompatibility and service life of the microelectrode. Besides, creating virtual electrodes by current steering technique increases the number of stimuli received by microelectrode during use, and improves its resolution in applications. Using current steering technique, the electric fields of adjacent electrodes interact in space to generate additional, perceptible, virtual stimuli between the stimuli produced by the two electrodes alone, that is, creating virtual electrode channels. This increases the number of stimuli received by microelectrode during use, and improves its resolution in applications, thereby broadening the application of microelectrode.

Secondly, the method for preparing microelectrode provided by the second aspect of the present invention is simple to operate, suitable for a large-scale preparation of microelectrode with uniform and stable performance.

Thirdly, the neural prosthesis provided by the present invention shows excellent performance and can be widely used in the fields of neurophysiology, brain science research and other life sciences.

BRIEF DESCRIPTION OF THE DRAWINGS

To illustrate the technical solutions in the embodiments of the present invention or in the prior art more clearly, the following briefly introduces the accompanying drawings required for describing the embodiments or the prior art. Apparently, the accompanying drawings in the following description show merely some embodiments of the present invention, and a person of ordinary skill in the art may still derive other drawings from these accompanying drawings without creative efforts.

DETAILED DESCRIPTION OF ILLUSTRATED EMBODIMENTS

The following describes preferred embodiments of the present invention. It should be noted that those skilled in the art can make several improvements or modifications without departing from the principles of the embodiments of the present invention. These improvements or modification are also considered as the protection scope of the present invention.

Figure 1:
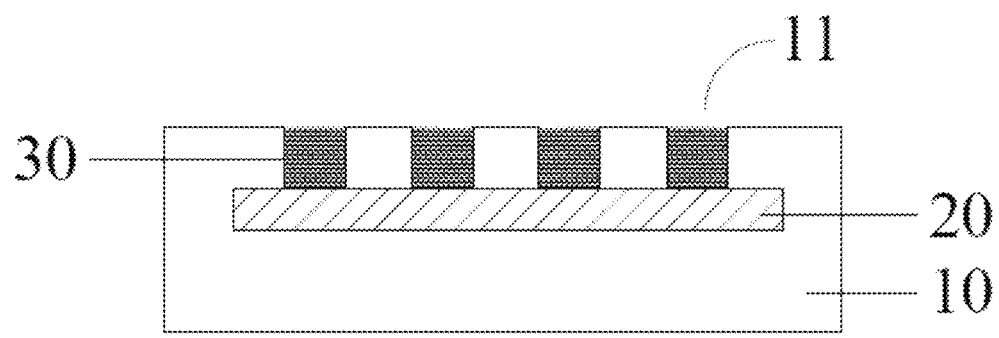
FIG. 1 is a schematic diagram showing the cross-sectional view of a microelectrode in accordance with an embodiment of the present invention.

Referring to FIG. 1, an exemplary microelectrode comprises a flexible layer 10, an electrically conductive layer 20 and a plurality of platinum dendrite structures 30, wherein the electrically conductive layer 20 is arranged in the flexible layer 10, wherein on the surface of the flexible layer 10 are a plurality of grooves 11 within which the electrically conductive layer 20 is revealed partially, and wherein each of the groove 11 is provided with one platinum dendrite structure 30 therein.

In the microelectrode provided by the present invention, the revealed electrically conductive layer 20 and the platinum dendrite structure 30 serve as a plurality of electrodes distributed uniformly, with smaller electrode sites and more electrodes and recording points, which brings intensive stimuli to nerve and overcomes the disadvantage of an ordinary planar electrode that the electrical lines of force diverge due to stronger edge electric field than the center electric field. The platinum dendrite structures 30 increase the surface area of the microelectrode and effectively improve the electrochemical performance of the microelectrode, such as reduced impedance, lower critical stimulating charge density, improved charge storage capacity and charge injection capacity, etc. Further, the platinum dendrite structures 30 are well combined with the electrically conductive layer 20, avoiding the shedding of the platinum dendrite structures 30 and improving the biocompatibility and service life of the microelectrode. Besides, creating virtual electrodes by current steering technique increases the number of stimuli received by microelectrode during use, and improves its resolution in applications. Using current steering technique, the electric fields of adjacent electrodes interact in space to generate additional, perceptible, virtual stimuli between the stimuli produced by the two electrodes alone, that is, creating virtual electrode channels. This increases the number of stimuli received by microelectrode during use, and improves its resolution in applications, thereby broadening the application of microelectrode.

In some embodiments, the flexible layer 10 has a thickness of 3 μm-300 μm. Further, the flexible layer 10 has a thickness of 10 μm-260 μm. In the present invention, material of the flexible layer 10 can be, but is not limited to, polyimide or parylene.

In some embodiments, the electrically conductive layer 20 has a thickness of 0.1 μm-100 μm. Further, the electrically conductive layer 20 has a thickness of 0.5 μm-80 μm.

In some embodiments, a distance between the plurality of grooves 11 is in a range of 10 μm-1000 μm. Further, the distance between the plurality of grooves 11 is in a range of 50 μm-700 μm. Furthermore, the distance between the plurality of grooves 11 is in a range of 80 μm-500 μm. In the present invention, the distance between the plurality of grooves 11 is selected to be beneficial to the creation of virtual electrode channels, thereby increasing the number of perceptions of the microelectrodes during use, and thus promoting resolution.

In some embodiments, the plurality of grooves 11 are arranged in an array. The array arrangement of the grooves 11 is beneficial to the array arrangement of the platinum dendrite structure 30 arranged in the grooves 11, thereby increasing the number of virtual channels created by the microelectrodes and increasing the number of stimuli.

In some embodiments, a shape of an opening of the groove can be, but is not limited to, a circle, a square, a rectangle, an ellipse, a diamond, or an irregular shape.

In some embodiments, the groove 11 has a depth of is 0.5 μm-80 μm. Further, the groove 11 has a depth of 2 μm-70 μm.

In some embodiments, a distribution density of the grooves 11 in the microelectrode is in a range of 10-300 grooves/cm². Further, the distribution density of the grooves 11 in the microelectrode is in a range of 50-200 grooves/cm².

In some embodiments, the platinum dendrite structure 30 consists of a plurality of platinum dendrites. Further, the platinum dendrite comprises at least one of platinum nanowires, platinum nanorods, platinum nanocones, and platinum nanoflowers. In the present invention, the platinum dendrite structures 30 greatly increase the surface area of the microelectrode, thereby improving its electrical performance.

In some embodiments, the platinum nanowires have a diameter of 2 nm-50 nm and a length of 0.2 μm-5 μm. Further, the platinum nanowires have a diameter of 3 nm-9 nm and a length of 1.2 μm-4 μm.

In some embodiments, the platinum nanorods have a diameter of 0.1 μm-1 μm and a length of 0.3 μm-5 μm. Further, the platinum nanorods have a diameter of 0.15 μm to 0.85 μm and a length of 0.8 μm to 4 μm.

In some embodiments, the bottom of the platinum nanocones has a diameter of 0.1 μm-1 μm, and the platinum nanocones have a height of 0.3 μm-5 μm. Further, the bottom of the platinum nanocones has a diameter of 0.2 μm-0.95 μm, and the platinum nanocones have a length of 1.5 μm-3.5 μm.

In some embodiments, the platinum nanoflowers have an average diameter of 0.2 μm-3 μm. Further, the platinum nanoflowers have an average diameter of 0.5 μm-2.6 μm. Further, each of the platinum nanoflowers comprises a plurality of platinum nanosheets, and the platinum nanosheets have a lateral dimension of 0.1 µm-1 µm. Furthermore, the platinum nanosheets have a lateral dimension of 0.15 µm-0.8 µm.

In some embodiments, the platinum nanowires, platinum nanorods, and platinum nanocones are selected to be beneficial to further increase the surface area of the microelectrode and improve its electrical performance.

In some embodiments, a distribution density of the platinum dendrites in the platinum dendrite structure 30 is in a range of 10 pcs/µm$^2$-300 pcs/µm$^2$. Further, the distribution density of the platinum dendrites in the platinum dendrite structure 30 is in a range of 25 pcs/µm$^2$-265 pcs/µm$^2$. Furthermore, the distribution density of the platinum dendrites in the platinum dendrite structure 30 is in a range of 50 pcs/µm$^2$-180 pcs/µm$^2$. In the present invention, the denser distribution of platinum dendrites will enable the microelectrode to have a larger surface area, thereby greatly improving the electrical performance and being more beneficial to its application. Specifically, a distribution density of the platinum dendrite may be, but is not limited to, 30 pcs/µm$^2$, 70 pcs/µm$^2$, 135 pcs/µm$^2$, or 180 pcs/µm$^2$.

In some embodiments, the platinum dendrite structure 30 has a thickness of 0.3 µm-70 µm. Further, the platinum dendrite structure 30 has a thickness of 3 µm-60 µm. Furthermore, the platinum dendrite structure 30 has a thickness of 5 µm-50 µm. In the present invention, the thickness of the platinum dendrite structure 30 is selected to be beneficial to the generation and transmission of stimuli. Specifically, the platinum dendrite structure 30 has a thickness of 0.8 µm, 2 µm, 8 µm, 25 µm, 36 µm, or 52 µm.

In some embodiments, a plurality of platinum dendrite structures 30 are arranged in an array such that an array of platinum dendrite structures is formed on the microelectrode, that is, a microelectrode array is formed. This arrangement further improves the overall electrical performance of the microelectrode and the number of stimuli received during use, increasing the number of virtual channels and promoting its resolution in applications.

In some embodiments, the platinum dendrite structure 30 may completely cover the bottom of the groove 11 (that is, the surface of the electrically conductive layer 20 revealed in each groove 11), or partially cover the bottom of the groove 11.

In some embodiments, the thickness of the platinum dendrite structure 30 may be equal to the depth of the groove 11, or less than the depth of the groove 11, or greater than the depth of the groove 11. In the embodiment where the thickness of the platinum dendrite structure 30 is greater than the depth of the groove 11, the surface area of the microelectrode is further increased, thereby improving its electrical performance.

In some embodiments, the revealed surface of the electrically conductive layer 20 is a flat surface or an uneven surface.

In some embodiments, an electrically conductive polymer layer is arranged on the platinum dendrite structure 30. The electrically conductive polymer layer is a soft material with excellent biocompatibility and good electrical properties, enabling it to fit tissues, reduce immune responses, and improve the long-term safety of microelectrode. Therefore, an electrically conductive polymer layer is arranged on the platinum dendrite structure 30 to combine "hard and soft material" to further improve the biocompatibility and service life of the microelectrode. In the present invention, the electrically conductive polymer layer may be arranged on all or some platinum dendrite structures. Further, in an embodiment where the electrically conductive polymer layer is arranged on all platinum dendrite structures, the biocompatibility and stability of the microelectrode is further improved.

In some embodiments, the electrically conductive polymer layer has a thickness of 0.1 µm-20 µm. Further, the electrically conductive polymer layer has a thickness of 2 µm-16 µm. In the present invention, the thickness of the electrically conductive polymer layer is selected to be beneficial to the transmission of stimuli of the electrically conductive layer 20 and the platinum dendrite structure 30. Specifically, the electrically conductive polymer layer may have a thickness of 0.5 µm, 3.6 µm, 8 µm, 14 µm, or 17 µm.

In some embodiments, the material of the electrically conductive polymer layer comprises at least one of polypyrrole, polyaniline, polythiophene and its derivatives, and electrically conductive hydrogel. That is, the material of the electrically conductive polymer layer comprises at least one of polypyrrole, polyaniline, polythiophene, polypyrrole derivatives, polyaniline derivatives, polythiophene derivatives and electrically conductive hydrogel. In the present invention, the material of the electrically conductive polymer layer is selected to be beneficial to the biocompatibility of the electrically conductive polymer layer, thereby improving the biocompatibility and safety of the microelectrode.

In some embodiments, the overall thickness of the platinum dendrite structure 30 and the electrically conductive polymer layer may be equal to the depth of the groove 11 or greater than the depth of the groove 11.

Figure 2:
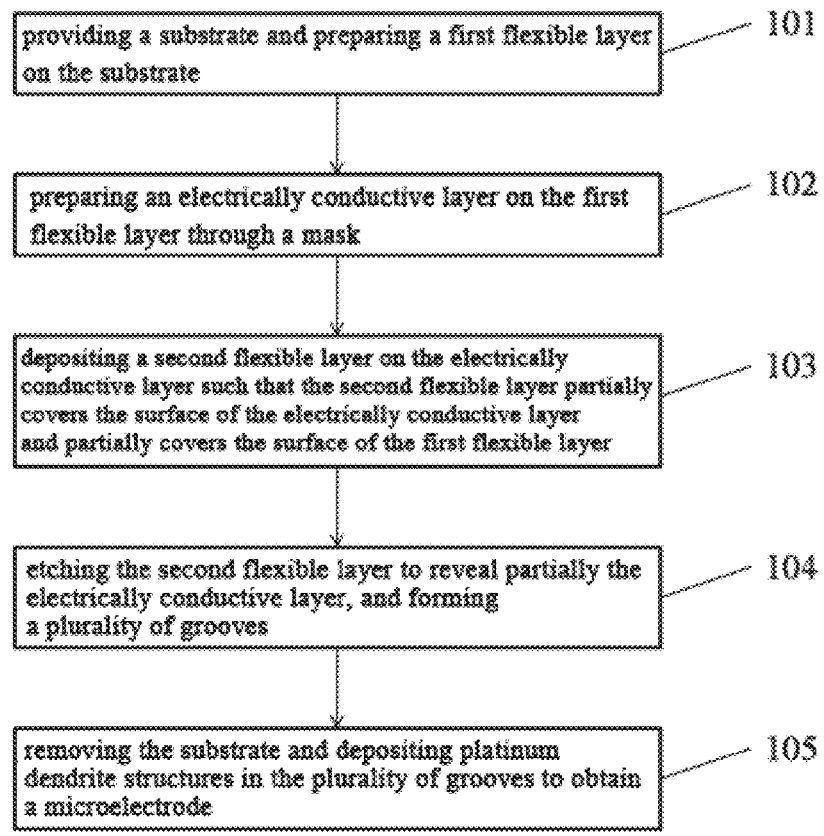
FIG. 2 is a flow chart of a method for preparing a microelectrode in accordance with an embodiment of the present invention.

Referring to FIG. 2, provided is an exemplary method for preparing a microelectrode comprising the following steps.

Step S101: providing a substrate and preparing a first flexible layer on the substrate.

Figure 3:
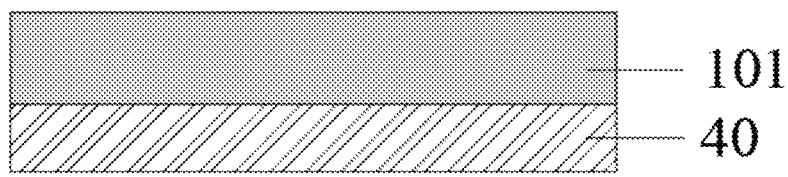
FIG. 3 is a schematic diagram showing step S101 in a method for preparing a microelectrode in accordance with an embodiment of the present invention.

Further referring to FIG. 3, a substrate 40 is provided. The substrate 40 may be, but is not limited to, a silicon wafer, a silicon oxide wafer or a glass wafer. The step of preparing a first flexible layer 101 on the substrate 40 comprises performing spin coating or deposition to prepare the first flexible layer 101 on the substrate 40. Alternatively, the material of the first flexible layer 101 may be, but is not limited to, polyimide or parylene. Alternatively, the first flexible layer 101 may have a thickness of 1 µm-200 µm.

Step S102: preparing an electrically conductive layer on the first flexible layer through a mask.

Figure 4:
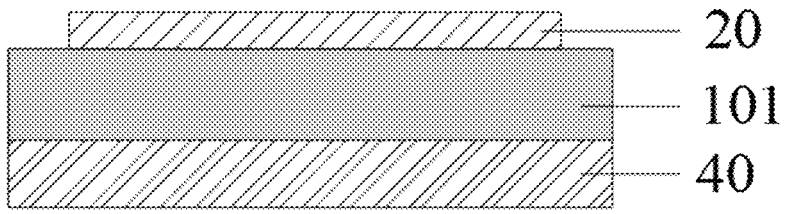
FIG. 4 is a schematic diagram showing step S102 in a method for preparing a microelectrode in accordance with an embodiment of the present invention.

Further referring to FIG. 4, an electrically conductive layer 20 is prepared on the first flexible layer 101 through a mask. Alternatively, this step comprises disposing a mask over the first flexible layer 101, and forming the electrically conductive layer 20 on the first flexible layer 101 by deposition such that the electrically conductive layer 20 partially covers the first flexible layer. Further, the deposition may be, but is not limited to, physical vapor deposition or chemical vapor deposition. Alternatively, the electrically conductive layer 20 has a thickness of 0.1 µm-100 µm.

Step S103: depositing a second flexible layer on the electrically conductive layer such that the second flexible layer partially covers the surface of the electrically conductive layer and partially covers the surface of the first flexible layer.

Figure 5:
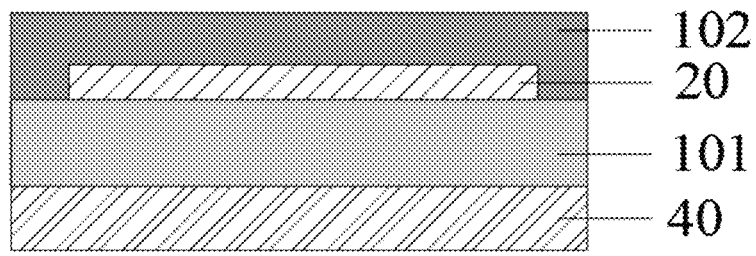
FIG. 5 is a schematic diagram showing step S103 in a method for preparing a microelectrode in accordance with an embodiment of the present invention.

Further referring to FIG. 5, a second flexible layer 102 is deposited on the electrically conductive layer 20. The second flexible layer 102 partially covers the surface of the electrically conductive layer 20 and partially covers the surface of the first flexible layer 101. Alternatively, the second flexible layer 102 is deposited on the electrically conductive layer 20 by spin coating or deposition. Alternatively, the material of the second flexible layer 102 may be, but is not limited to, polyimide or parylene. Alternatively, the second flexible layer 102 has a thickness of 1 μm-200 μm.

Step S104: etching the second flexible layer to reveal partially the electrically conductive layer, and forming a plurality of grooves.

Figure 6:
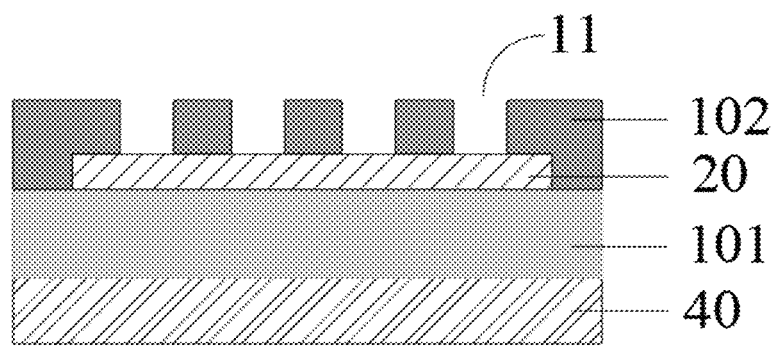
FIG. 6 is a schematic diagram showing step S104 in a method for preparing a microelectrode in accordance with an embodiment of the present invention.

Further referring to FIG. 6, the second flexible layer 102 is etched to partially reveal the electrically conductive layer 20 and form a plurality of grooves 11. Alternatively, the etching comprises at least one of dry etching and wet etching. Specifically, the etching may be, but is not limited to, reactive ion etching and plasma etching. In one embodiment, reactive ion etching (Reactive Ion Etching, RIE) is performed to deposit an aluminum mask on the second flexible layer 102 to form a plurality of grooves 11, followed by performing wet etching to remove the aluminum mask. In the present invention, the thickness of the platinum dendrite structure 30 may be equal to the depth of the groove 11, or less than the depth of the groove 11, or greater than the depth of the groove 11. In one embodiment where the thickness of the platinum dendrite structure 30 is greater than the depth of the groove 11, the surface area of the microelectrode is further increased, thereby improving its electrical performance. The distance between adjacent grooves 11 may be the same or different. Alternatively, the distance between adjacent grooves 11 is in a range of 10 μm-1000 μm. Further, the distance between adjacent grooves 11 is in a range of 50 μm-700 μm. Furthermore, the distance between adjacent grooves 11 is in a range of 80 μm-500 μm. In the present invention, the distance between the plurality of grooves 11 is selected to be beneficial to the creation of virtual electrode channels, thereby increasing the number of perceptions of the microelectrodes during use, and thus promoting resolution. In the present invention, a shape of an opening of the groove 11 can be, but is not limited to, a circle, a square, a rectangle, an ellipse, a diamond, or an irregular shape. In the present invention, the revealed surface of the electrically conductive layer 20 is a flat surface or an uneven surface. That is, when etching the second flexible layer, part of the second flexible layer is completely etched to reveal part of the electrically conductive layer, i.e. the revealed surface of the electrically conductive layer is a flat surface, or both part of the second flexible layer and part of the electrically conductive layer are etched to reveal part of the electrically conductive layer, i.e. the revealed surface of the electrically conductive layer is an uneven surface.

Step S105: removing the substrate and depositing platinum dendrite structures in the plurality of grooves to obtain a microelectrode.

Figure 7:
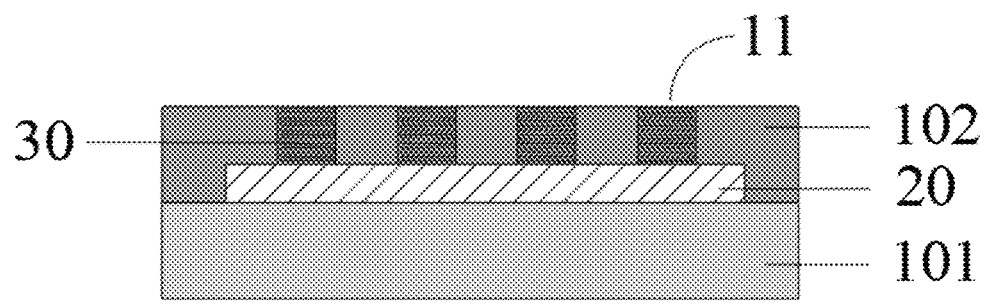
FIG. 7 is a schematic diagram showing step S105 in a method for preparing a microelectrode in accordance with an embodiment of the present invention.

Further, referring to FIG. 7, the substrate 40 is removed, and the platinum dendrite structures 30 are deposited in the plurality of grooves 11 to obtain a microelectrode. Alternatively, the step of depositing platinum dendrite structures 30 in the plurality of grooves 11 comprises: providing a platinum salt solution, performing constant potential deposition or constant current deposition to form the platinum dendrite structures 30 in the plurality of grooves 11. Further, the platinum salt comprises at least one of platinum chloride, ammonium hexachloroplatinate, potassium hexachloroplatinate, sodium hexachloroplatinate, chloroplatinic acid, platinum nitrate, platinum sulfate, potassium tetrachloroplatinate and ammonium tetrachloroplatinate. Further, the platinum salt solution has a concentration greater than 30 mmol/L. Further, the platinum salt solution has a pH of 7-8. Further, the method further comprises pretreating the grooves 11, before performing constant potential deposition or constant current deposition to form the platinum dendrite structures 30 in the plurality of grooves 11. Further, the step of pretreating comprises cleaning and roughening the grooves 11. Pretreatment on the grooves 11 will improve the bonding between the grooves 11 and platinum dendrite structure 30 subsequently deposited therein such that the platinum dendrite structure 30 will not readily fall off the grooves 11. Further, the constant potential deposition may be performed at a potential of −0.6V to −0.75V for 20 min to 60 min. Further, the constant current deposition may be performed at a current of −2 μA to −5 μA for 20 min to 60 min. In this embodiment, the first flexible layer 101 and the second flexible layer 102 are depicted as the flexible layer 10 in FIG. 1. In the present invention, the substrate may be removed first, followed by depositing the platinum dendrite structures, or the platinum dendrite structures may be deposited first, followed by removing the substrate.

Figure 8:
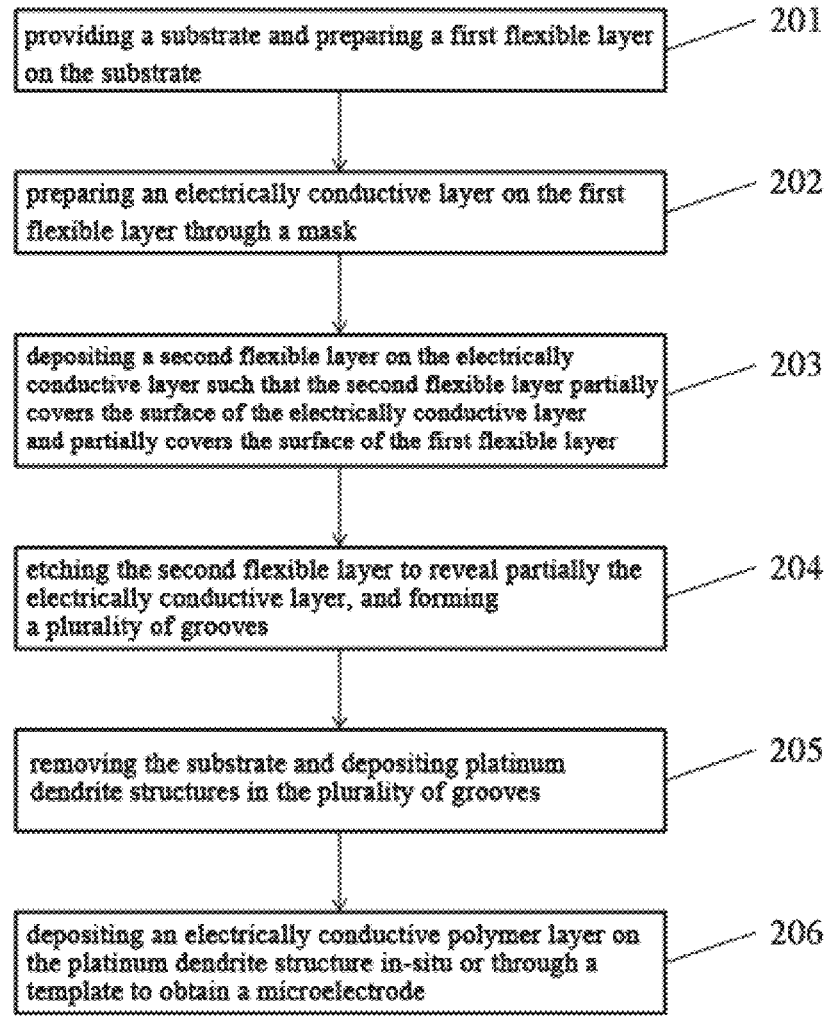
FIG. 8 is a flowchart of a method for preparing a microelectrode in accordance with another embodiment of the present invention.

Referring to FIG. 8, provided is a flowchart of a method for preparing a microelectrode in accordance with another embodiment of the present invention. Steps S201-S205 are the same as S101-S105 of the above-mentioned embodiment, and further included is step S206: depositing an electrically conductive polymer layer on the platinum dendrite structure in-situ or through a template to obtain a microelectrode. Alternatively, the electrically conductive polymer layer has a thickness of 0.1 μm-20 μm. Further, the electrically conductive polymer layer has a thickness of 2 μm-16 μm. The overall thickness of the platinum dendrite structure 30 and the electrically conductive polymer layer may be equal to the depth of the groove 11 or greater than the depth of the groove 11. In the present invention, the thickness of the electrically conductive polymer layer is selected to be beneficial to the transmission of stimuli of the electrically conductive layer 20 and the platinum dendrite structures 30. Alternatively, the material of the electrically conductive polymer layer comprises at least one of polypyrrole, polyaniline, polythiophene and its derivatives, and electrically conductive hydrogel. That is, the material of the electrically conductive polymer layer comprises at least one of polypyrrole, polyaniline, polythiophene, polypyrrole derivatives, polyaniline derivatives, polythiophene derivatives and electrically conductive hydrogel. In the present invention, the material of the electrically conductive polymer layer is selected to be beneficial to the biocompatibility of the electrically conductive polymer layer, thereby improving the biocompatibility and safety of the microelectrode. The electrically conductive polymer layer is a soft material with excellent biocompatibility and good electrical properties, enabling it to fit tissues, reduce immune responses, and improve the long-term safety of microelectrode. Therefore, an electrically conductive polymer layer is arranged on the platinum dendrite structure 30 to combine "hard and soft material" to further improve the biocompatibility and service life of the microelectrode.

Figure 9:
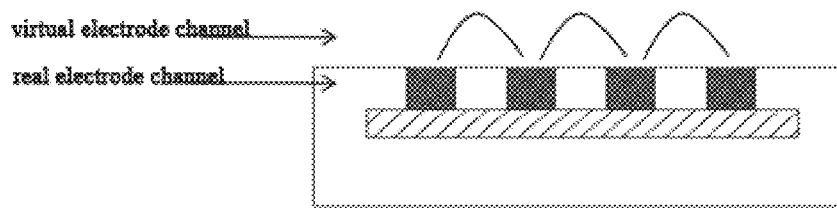
FIG. 9 is a schematic diagram of electrode channels of a microelectrode in accordance with the present invention.

The present invention also provides a neural prosthesis comprising the above-mentioned microelectrode. In the present invention, the neural prosthesis can be, but is not limited to, a cochlear implant, an optic nerve prosthesis, an implantable cardiac pacemaker or an implantable deep brain stimulator. Specifically, in an embodiment where the neural prosthesis is an optic nerve prosthesis, it has good electrical performance and biocompatibility. On the other hand, as shown in FIG. 9, the multi-focus electrodes in the microelectrode realizes the multiple stimulation of real electrode channel and virtual electrode channel and precise nerve regulation, thus improving spatial resolution and providing hardware basis for high-density nerve stimulation and neural prosthesis. For the microelectrode provided by the present invention, the stimulus waveform, amplitude, and charge distribution on different electrode pairs are changed through controlling the electric field. Specifically, the distribution of the stimulus charges of adjacent or spaced electrode points may, but is not limited to, increase from 0 to 1 at an increment of 0.1. It is possible to realize the dynamic movement of the stimuli focus due to the directional flow of electric current, thereby creating virtual channels. This may realize multi-channel virtual stimulation in a limited microelectrode space and improve the stimulation effect. In the present invention, the neural prosthesis comprises one or more of the above-mentioned microelectrodes. Specifically, in one embodiment where the neural prosthesis comprises a plurality of microelectrodes, the plurality of microelectrodes are arranged in an array, which is more conducive to increasing the number of received stimuli during the use of the neural prosthesis and significantly improving the resolution.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A method for fabricating a microelectrode, comprising:
   providing a substrate and depositing a first flexible layer on the substrate;
   depositing an electrically conductive layer on the first flexible layer through a mask;
   depositing a second flexible layer on the electrically conductive layer such that the second flexible layer partially covers a surface of the electrically conductive layer and partially covers a surface of the first flexible layer;
   etching the second flexible layer to form a plurality of grooves in which the electrically conductive layer is partially exposed; and
   removing the substrate and depositing platinum dendrite structures in the plurality of grooves such that a bottom of each of the plurality grooves is completely covered by the platinum dendrite structures to obtain the microelectrode;
   wherein the plurality of grooves and the platinum dendrite structures are arranged in an array, and
   wherein each of the first flexible layer and the second flexible layer comprises polyimide or parylene.

2. The method for fabricating a microelectrode of claim 1, further comprising depositing an electrically conductive polymer layer on the platinum dendrite structures in-situ or through a template, after depositing the platinum dendrite structures in the plurality of grooves.

3. The method for fabricating a microelectrode of claim 1, wherein the step of depositing platinum dendrite structures in the plurality of grooves comprises:
   providing a platinum salt solution,
   performing constant potential deposition or constant current deposition to form the platinum dendrite structures in the plurality of grooves.

4. The method for fabricating a microelectrode of claim 3, wherein the platinum salt solution comprises at least one of platinum chloride, ammonium hexachloroplatinate, potassium hexachloroplatinate, sodium hexachloroplatinate, chloroplatinic acid, platinum nitrate, platinum sulfate, potassium tetrachloroplatinate and ammonium tetrachloroplatinate.

5. The method for fabricating a microelectrode of claim 3, wherein the platinum salt solution has a concentration greater than 30 mmol/L.

\* \* \* \* \*